United States Patent
Kawasaki et al.

(10) Patent No.: US 8,436,899 B2
(45) Date of Patent: May 7, 2013

(54) METHOD AND APPARATUS OF TILTED ILLUMINATION OBSERVATION

(75) Inventors: Takeshi Kawasaki, Musashino (JP); Tomonori Nakano, Kodaira (JP); Kotoko Hirose, Abiko (JP)

(73) Assignee: Hitachi High-Technologies Corporation, Tokyo (JP)

( * ) Notice: Subject to any disclaimer, the term of this patent is extended or adjusted under 35 U.S.C. 154(b) by 825 days.

(21) Appl. No.: 12/535,021

(22) Filed: Aug. 4, 2009

(65) Prior Publication Data

US 2010/0033560 A1  Feb. 11, 2010

(30) Foreign Application Priority Data

Aug. 6, 2008 (JP) ................................. 2008-203196

(51) Int. Cl.
*H04N 7/18* (2006.01)

(52) U.S. Cl.
USPC .......................................................... 348/126

(58) Field of Classification Search .................... 348/126
See application file for complete search history.

(56) References Cited

U.S. PATENT DOCUMENTS

| 6,140,644 | A | 10/2000 | Kawanami et al. |
| 6,545,275 | B1 | 4/2003 | Pearl et al. |
| 6,809,809 | B2 * | 10/2004 | Kinney et al. ............... 356/237.5 |
| 6,812,462 | B1 * | 11/2004 | Toth et al. ........................ 850/1 |
| 7,034,297 | B2 * | 4/2006 | Petrov et al. ................... 250/310 |
| 7,598,491 | B2 * | 10/2009 | Fukunishi et al. ............ 250/310 |
| 7,897,936 | B2 * | 3/2011 | Shichi et al. ............. 250/442.11 |
| 2004/0119022 | A1 | 6/2004 | Sato et al. |
| 2004/0173746 | A1 * | 9/2004 | Petrov et al. ................... 250/310 |
| 2005/0133718 | A1 | 6/2005 | Miyamoto et al. |
| 2006/0033037 | A1 | 2/2006 | Kawasaki et al. |
| 2006/0097184 | A1 * | 5/2006 | Frosien ...................... 250/396 R |
| 2006/0289752 | A1 * | 12/2006 | Fukunishi et al. ............ 250/310 |
| 2006/0289757 | A1 * | 12/2006 | Kochi et al. ................... 250/310 |
| 2007/0158567 | A1 | 7/2007 | Nakamura et al. |
| 2007/0187595 | A1 * | 8/2007 | Tanaka et al. ................. 250/307 |
| 2007/0262255 | A1 * | 11/2007 | Feuerbaum .................... 250/307 |
| 2008/0237456 | A1 * | 10/2008 | Miyamoto et al. ......... 250/252.1 |
| 2008/0296498 | A1 * | 12/2008 | Hong ............................ 250/311 |
| 2010/0140470 | A1 * | 6/2010 | Shachal ........................ 250/307 |

FOREIGN PATENT DOCUMENTS

| JP | 11-40096 | 2/1999 |
| JP | 2001-202911 | 7/2001 |
| JP | 2005-183369 | 7/2005 |

(Continued)

OTHER PUBLICATIONS

F. Zemlin et al., "Coma-Free Alignment of High Resolution Electron Microscopes With the Aid of Optical Diffractograms", Ultramicroscopy 3 (1978) 49-60, North-Holland Publishing Company.

*Primary Examiner* — Duyen Doan
(74) *Attorney, Agent, or Firm* — Antonelli, Terry, Stout & Kraus, LLP.

(57) ABSTRACT

A tilted illumination observation method and observation device with easy adjustment, high speed, good reproducibility and low cost is provided. A high resolution tilt image of a specimen is obtained by extracting the blurring on the scanning spot occurring during beam tilt from the image (step 6) captured by the tilted beam, and the image (step 4) captured from directly above the standard specimen; and then deconvoluting (step 11, 12) the tilted image of the target specimen (step 10) using the extracted scanning spot from the oblique beam.

10 Claims, 4 Drawing Sheets

FOREIGN PATENT DOCUMENTS

| | | |
|---|---|---|
| JP | 2006-054074 | 2/2006 |
| JP | 3968334 | 6/2007 |
| JP | 2007-173132 | 7/2007 |
| JP | 2008-159286 | 7/2008 |

\* cited by examiner

METHOD AND APPARATUS OF TILTED ILLUMINATION OBSERVATION

CLAIM OF PRIORITY

The present application claims priority from Japanese patent application JP 2008-203196 filed on Aug. 6, 2008, the content of which is hereby incorporated by reference into this application.

FIELD OF THE INVENTION

The present invention relates to a charged particle beam apparatus, and relates in particular to tilted illumination observation technology such as for microscopes, inspection apparatuses, length measurement apparatuses and machining apparatuses for scanning a focused charged particle beam on the specimen surface.

BACKGROUND OF THE INVENTION

Along with progress made in recent years in reducing the size of semiconductors, a new type semiconductor possessing a three-dimensional structure such as the Fin Field Emission Transistor (FinFET) has started to appear. Along with these new type semiconductors, the critical dimension measurement devices and scanning devices used for semiconductor production and research require the capability to observe in fine detail three-dimensional shapes such as the bottom surface of concavities and device sidewalls whose angles are nearly perpendicular and therefore difficult to view during observation from directly above. Scanning electron microscopes (SEM) that utilize an electron beam are used for the purpose of length measurement and semiconductor inspection where high resolution capability is needed. Critical dimension scanning electron microscopes (CD-SEM) for example, possess a high resolution of approximately 2 nm at an acceleration voltage of 1 kilovolt or lower. Observing the above described three-dimensional shapes in this type of devices, requires tilted illumination observation that views from an oblique position rather than viewing from directly above.

The tilted illumination observation method is considered a technique where: (1) the specimen stage is set to be inclined, (2) the SEM column is set to be inclined, (3) a separate tilted illumination observation column is installed, and (4) a beam is irradiated at an oblique angle, etc. Among these steps, (1) through (3) require a special mechanical mechanism. In the case of (4), a primitive tilted illumination causes the blurring of the beam, so there is a loss of resolution. Whereupon methods to correct this blurring included (4a) installing a compensator device (See JP-A-2006-54074), and (4b) making adjustments of the astigmatism, focus and aperture position, so as to cancel out aberrations due to the beam inclination (See Japanese Patent No. 3968334).

A method has been proposed for making precise measurements of the beam tilt angle by using a specimen whose structure is known (See JP-A-2005-183369). The beam tilt angle must be accurately known in order to enhance the accuracy of the three-dimensional reconstruction assembled from multiple tilted beam images.

Though not specifically intended for tilted illumination observation, a technique to measure aberrations of the lens by using the beam inclination was developed for the transmission electron microscope (TEM) (Ultramicroscopy Vol. 3, 1978, pp. 49-60).

Moreover, a technology that adjusted deviations in aberration correction conditions was disclosed in JP-A-2007-173132. When image shifting function is used in Cs corrected scanning transmission electron microscopes (STEM), there is a possibility that the aberration correction condition is changed. By extracting the electron beam spot shapes from the tilt scanning transmission images of the specimen, using the deconvolution method and arranging these spot shapes in a tableau shape according to the tilt azimuth, it is possible to detect the deviation in aberration conditions from the symmetry of the tableau. Then correcting the deviation in aberration compensation conditions by using a two-stage deflector device to adjust the deflection center point. This technology for forming the tilted electron beam is at most a technique for adjusting the Cs corrected STEM, and intended if the adjustment goes well, to ultimately obtain a high resolution image with a vertical incident beam. This technology requires multiple tilt azimuths, and moreover, it is necessary to evaluate the symmetry of the tableau.

However, the technique described above in (1) through (3) need to incline the specimen stage or the SEM column, so the distance between the specimen and the objective lens cannot be narrowed in order to secure the space. Moreover, resolution improvement technique using a retarding electrical field cannot be utilized, because the specimen and the objective lens are not placed in parallel during tilt observation. As a result, resolution is inferior in the tilt observation compared with the top down observation. Further, problems are that it costs to add the hardware of the specimen tilt mechanism, it takes time to the tilt operation; therefore, the observation throughput deteriorates when frequently performing tilted illumination observation.

The technology in (4a) an aberration corrector removes aberrations increasing via the tilt so that high resolution during tilting it theoretically possible but has the problem that current compensator devices are expensive and the adjustment technique is complex. The technology in (4b) is theoretically incapable of restoring the resolution even if using methods such as shifting the aperture or electro-optically adjusting the axis so as to decrease the blurring of the scan spot caused by the tilted beam irradiation. A particular problem is that the resolution deteriorates drastically when the tilt angle reaches several degrees, compared to observation from right above. Also, techniques such as switching frequently between tilted illumination observation and observation from right above to compare the images are difficult for adjusting many parts of column and have difficulty in reproducibility.

Moreover, even if the beam tilt angle can be measured with some accuracy, the resolution of the tilted image is poor, so it is inevitable to improve the solution to rebuild the three-dimensional image.

In order to resolve the above problems of the conventional art, the present invention has the object of providing an easily adjustable tilted illumination observation method possessing high speed, good reproducibility and a low cost, as well as a device using that method for restoring the resolution by image processing after blurring of the image during tilted illumination observation, to a resolution equivalent to observation from directly above.

SUMMARY OF THE INVENTION

In order to achieve the above objects, the tilted illumination observation method for observing an observation specimen, comprises directing a focused charged particle beam to scan a standard specimen; detecting reflected particles or secondary particles emitted from the standard specimen; obtaining a perpendicular irradiation image of the standard specimen; obtaining a first tilted irradiation image of the standard specimen; directing a focused charged particle beam to scan an observation specimen; detecting reflected particles or secondary particles emitted from the observation specimen; obtaining a second tilted irradiation image of the observation specimen under the same condition used to obtain the first tilted irradiation image; and obtaining an image that compensates for blurring of the second tilted irradiation image by utilizing the perpendicular irradiation image and the first tilted irradiation image.

To further achieve the above objects, the observation device to observe an observation specimen by utilizing an image obtained by detecting secondary particles or reflected particles emitted from the observation specimen due to irradiating the observation specimen with a focused charged particle beam, the observation device comprises a charged particle source to supply a charged particle beam; a condenser lens unit to control the focus position and the focus angle of the charged particle beam emitted from the charged particle source; an objective lens unit to converge the charged particle beam onto the observation specimen; a scanning unit to scan the charged particle beam onto the observation specimen at a desired tilt angle; an image acquisition unit to detect the secondary particles or the reflected particles emitted from the observation specimen and a standard specimen, and acquire images synchronized with the scanning by the charged particle beam; an image processor unit to correct blurring of an image of the observation specimen obtained with the charged particle beam during tilted irradiation, by using a first image of the standard specimen acquired by tilted irradiation and a second image of the standard specimen acquired by perpendicular irradiation; and a display unit to display a corrected image of the observation specimen.

Namely, this invention extracts the blurring from the scanning spot during tilted illumination observation by deconvolution from the two images made up of the image taken from right above the reference specimen and the image acquired with the tilted beam, and improves the resolution of the tilt image by once again deconvoluting the spot extracted during tilt.

This invention is capable of restoring the image resolution in speedy and simple tilted illumination observation and thereby attaining accurate three-dimensional observation.

DETAILED DESCRIPTION OF THE PREFERRED EMBODIMENTS

Figure 1:
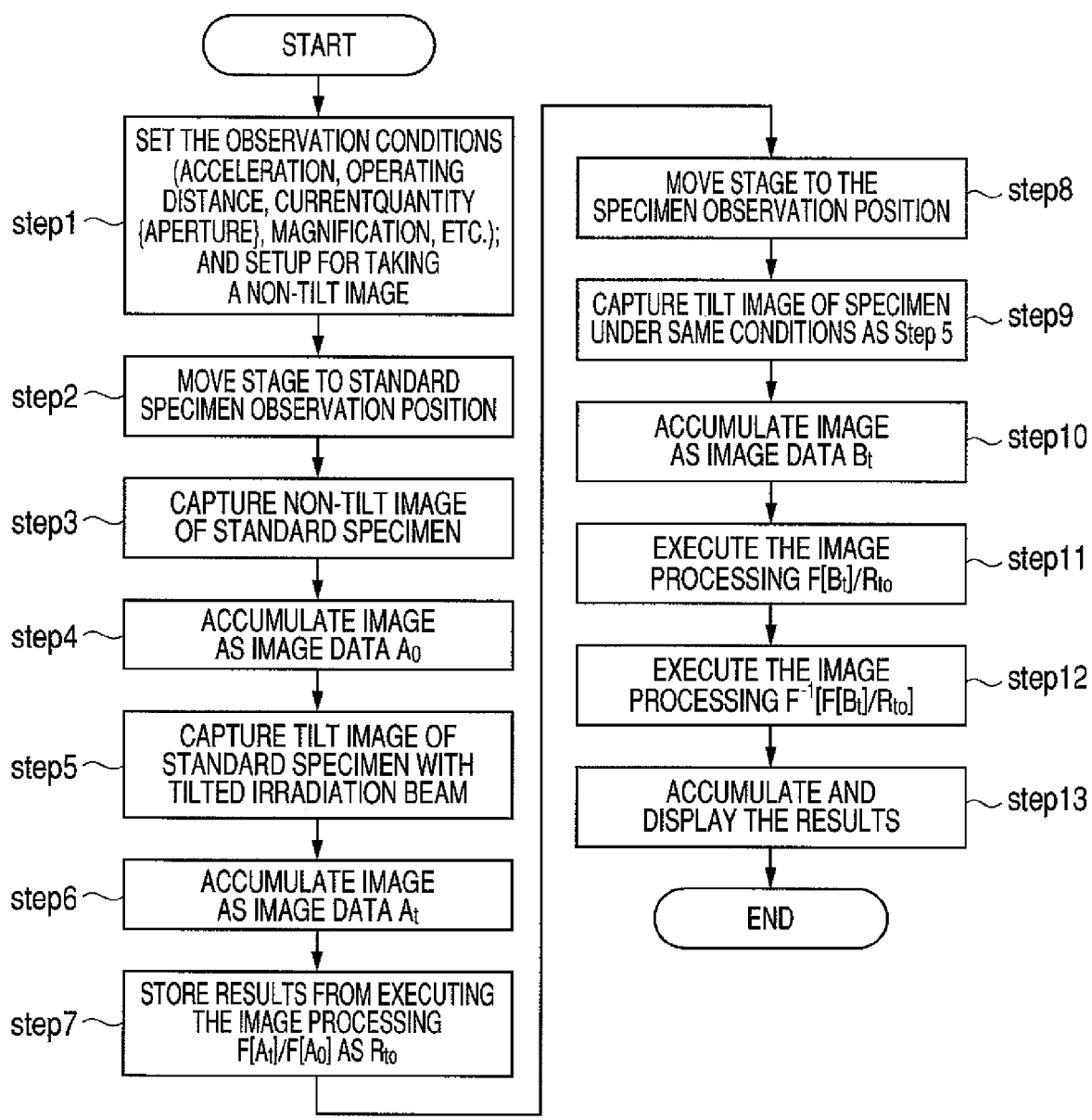
FIG. 1 is a drawing showing the procedure for obtaining a high resolution tilt image by the observation method of the first embodiment.

Prior to describing the best embodiments for implementing this invention, the principle of the present invention is described using mathematical formulas.

Namely, the resolution of the tilt image can specifically be improved by the following process.

The SEM forms an image captured with the secondary electrons or the reflected electrons generated during scanning on the specimen with the primary electron beam. The convolution of the spot intensity S and distribution coefficient A of secondary electron and reflected electron emissions from the specimen is mathematically described as follows:

$$A(x, y) = \iint S(u, v)A(x-u, y-v)dudv = S \otimes A \quad (1)$$

Here, separating the tilt irradiation and the non-tilt irradiation respectively into the tilt irradiation image At, and the non-tilt irradiation image $A_0$ yields, $$At = S(\text{tilt}) \otimes A(\text{tilt}) \quad (2)$$

$$A_0 = S(0) \otimes A(0) \quad (3)$$

If evaluating for example fine gold particles on a flat carbon substrate as the standard specimen, then there is little significant difference in the state of the secondary electron or reflected electron emissions for a distribution function A, whether in the case of tilt irradiation or non-tilt irradiation and therefore we obtain the following.

$$A(\text{tilt}) \approx A(0) \quad (4)$$

However, the intensity distribution S of the spot changes due to effects from the aberration and so we obtain as follows.

$$S(\text{tilt}) \neq S(0) \quad (5)$$

More specifically, the S(tilt) becomes drastically blurred due to focus deviations, astigmatisms, coma astigmatisms and chromatic dispersion so that the resolution of the tilt image (2) also deteriorates. Performing Fourier conversion of the tilt irradiation image and the non-tilt irradiation image of this standard specimen and then dividing allows obtaining as follows from the mathematical properties of convolution.

$$F[At]/F[A_0] = F[S(\text{tilt}) \otimes A(\text{tilt})]/F[S(0) \otimes A(0)] = (F[S(\text{tilt})]F[A(\text{tilt})])/(F[S(0)]F[A(0)]) = F[S(\text{tilt})]/F[S(0)] \quad (6)$$

Here, however formula (4) was used on the standard specimen.

Whereupon in order to restore the resolution in the tilt image for the target specimen B, $$Bt = S(\text{tilt}) \otimes B(\text{tilt}) \quad (7)$$

we divide the Fourier transform of (7) by the formula (6).

$$F[Bt]/\{F[S(\text{tilt})]/F[S(0)]\} = F[S(\text{tilt}) \otimes B(\text{tilt})]/\{F[S(\text{tilt})]/F[S(0)]\} = F[S(0) \otimes B(\text{tilt})] \quad (8)$$

and by then finding the inverse Fourier transform of (8), we obtain.

$$F^{-1}F[S(0) \otimes B(\text{tilt})] = S(0) \otimes B(\text{tilt}) \quad (9)$$

A tilt image of specimen B scanned by the non-tilt beam S(0) having no blurring, or in other words, a tilted illumination observation image whose resolution is restored, is obtained in this way. Moreover, the S(tilt) also contains beam blurring due to chromatic dispersion during the beam tilting, so the image will theoretically also be restored by this processing.

Fourier transforms of images $A_0$, At of the standard specimen were used here however, processing via a cross-correlation function for $A_0$, At can be utilized if the non-tilt beam spot is drastically smaller than the specimen B structure. This processing is possible because defining the cross-correlation function as:

$$C \circ D = \iint C(u, v)D(u+x, v+y)dudv \quad (10)$$

Yields, $$F[C \circ D] = (F[C])^*(F[D]) \quad (11)$$

Resulting in, $$F[A_0 \circ At]=(F[A_0])^*(F[At])=(F[S(0)]F[A(0)])^*(F[S(tilt)]F[A(tilt)])=F[S(0)] \circ S(tilt)]F[A(0) \circ A(tilt)] \approx F[S(0)]^*F[S(tilt)] \quad (12)$$

Here, we assume the following.

$$F[A(0) \circ A(tilt)]=F[A(0) \circ A(0)] \approx const \quad (13)$$

Moreover, instead of formula (8), we calculate, $$F[Bt]/\{F[A_0 \circ At]\}=F[S(tilt)]F[B(tilt)]/\{F[S(0)]^*F[S(tilt)]\} \approx F[S(0) \otimes B(tilt)] \quad (14)$$

and use the inverse Fourier transform of (14) to find (9).

Here, the following formula was assumed.

$$F[S(0) \circ S(0)]=F[S(0)]^*F[S(0)] \approx const \quad (15)$$

A Fourier transform of the SEM image is used in the subsequent image processing so when making the Fourier transform, the object serving as the standard specimen should allow power to be distributed across a wide range of spatial frequencies. In other words, an object structure with clearly defined edges on the specimen and with a mix of edges large and small in all directions is preferable. Gold particles, latex balls, platinum particles, aluminum particles, silicon particles on carbon; as well as patterns on substrates made up of combinations of repeating patterns such as straight lines, circles, squares and triangles are for example satisfactory. Vaporized gold particles in sizes spanning approximately 5 nm to 100 nm for may be used for high magnifications up to 200,000 times, and patterns with combinations of circular and polygons in sizes from approximately 100 nm to 500 nm on the substrate can be utilized for low magnifications of 50,000 or less.

The optimal embodiments of this invention are described next for the case of a scanning microscope (SEM) utilizing electrons as the charged particles. Needless to say, the scanning microscope utilizing other charged particles such as ions may theoretically be utilized in the same way.

First Embodiment

The procedure in the tilted illumination observation method of the first embodiment for acquiring a tilt high resolution image is described while referring to FIG. 1.

The operator first of all decides the SEM observation conditions (acceleration voltage, working distance: WD, electrical current quantity, and magnification, etc.) and sets a state for capturing non-tilt images (STEP 1). The specimen stage is next shifted to the standard specimen position built into a section of the specimen stand (STEP 2). An image is then captured at the magnification that the operator wants to observe the non-tilt irradiation image of the standard specimen (STEP 3). This image is accumulated as image data $A_0$ in the memory unit. An optional name may be used as the name of the image from here onwards (STEP 4).

The beam is then tilted to acquire a tilt image of the standard specimen (STEP 5). If the beam tilt angle and azimuth must be found because three-dimensional processing or other tasks are planned later on; then the beam tilt angle and azimuth are measured beforehand using a specimen with a known geometric shape such as a pyramid-shaped specimen. If the accurate tilt angle or azimuth is not needed for subsequent image interpretation then the process can proceed without finding the beam tilt angle and azimuth. A reproducible beam tilt is sufficient. The acquired tilt image is then accumulated as the image data At in the memory unit (STEP 6).

The above described image processing (6) is then executed as $F[At]/F[A_0]$ where F is defined as the processing of the Fourier transform, and the results are accumulated in the memory unit as Rto (STEP 7). The pre-processing for the Fourier transform is here implemented by utilizing an appropriate filter such as a Hanning filter, and processing to suppress false images and noise may also be performed. In some cases, rather than division of the image Fourier transform, the processing (11) for the At, $A_0$ cross correlation just as described above may be substituted. Even in the image processing from here onwards, cross-correlation processing may be substituted for use of filters or Fourier conversion.

The stage is next moved and the visual field aligned with the section of the specimen the operator wants to view (STEP 8). A tilt image of the specimen is next captured under the same tilt irradiation conditions as in STEP 5 (STEP 9). This tilt image is then accumulated in the memory section as the image data Bt of processing (7) (STEP 10).

The image processing F[Bt]/Rto is then performed just as shown in the arithmetic expression (8) (STEP 11). An inverse Fourier transform (9) is next performed by using the results in STEP 11 and an image acquired (STEP 12). Finally, the acquired tilt high resolution image is displayed, and after accumulating the image in the memory section, the process terminates (STEP 13).

The sequence from STEP 8 to STEP 13 can be repeated if the operator wants to observe the specimen under the same tilt irradiation conditions but under a different visual field. Moreover, if the position coordinates for the location where the observation must be made is known in advance, then those coordinates can be utilized for automated control of the specimen stage and automated measurements using a critical dimension (CD) SEM, etc.

Restart the sequence from STEP 1 if changing the tilted illumination observation conditions. However if a number of tilt irradiation conditions are already decided for observation, then images can be captured first for the standard specimen from STEP 5 through STEP 7 for example for combinations of multiple tilt conditions such as azimuth 0°, 45°, 90°, 135°, 180°, 225°, 270°, 315°, and tilt angles 3°, 5°, 10°, 15°, and so on. These images can then be stored in the memory unit. Necessary current conditions can be selected for specimens at an appropriate later time from among the multiple stored tilt conditions and images then captured.

Figure 2:
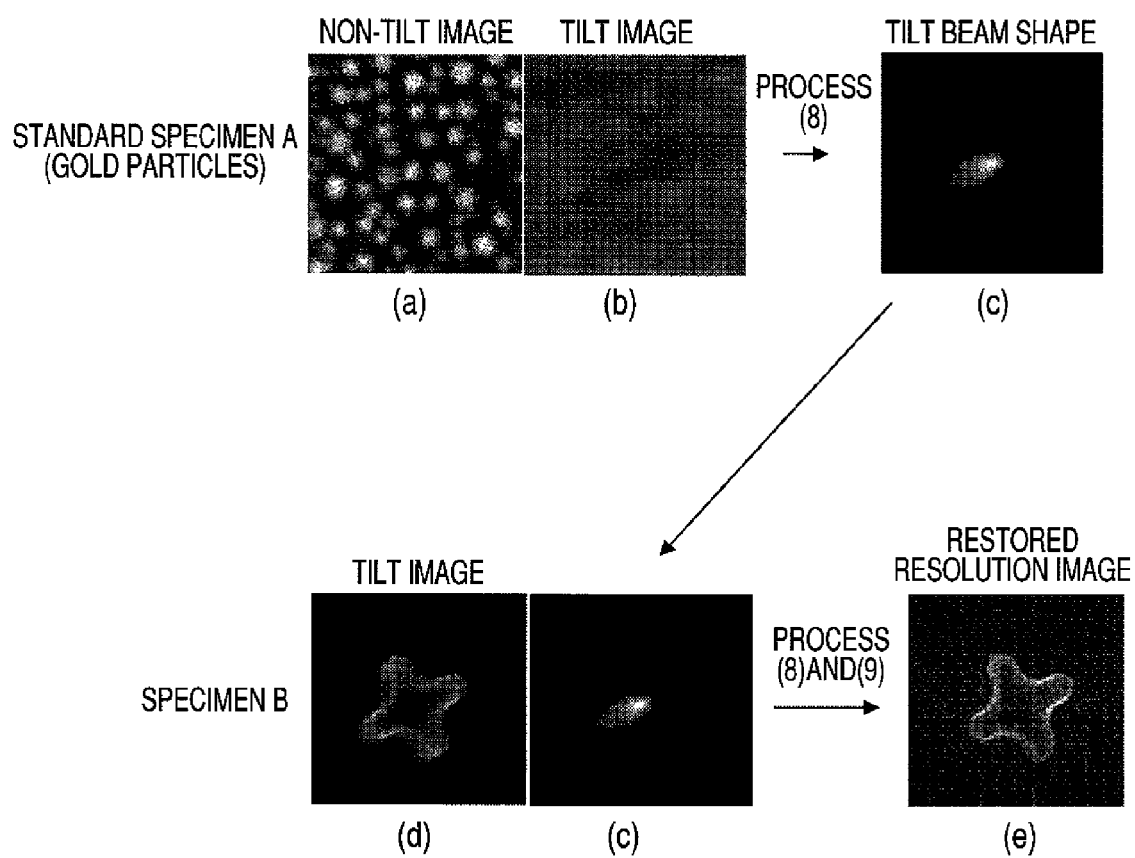
FIG. 2 is an example of restoring the resolution of the tilt image by the observation method of the first embodiment.

FIG. 2 is photographs showing examples of tilt resolution images obtained from actual tilt SEM images using the sequence for the above described observation method of the first embodiment.

Here, the scanning beam contour (c) is found from the tilt image (b) and the non-tilt image (a) from standard specimen A (gold particles on carbon), and high resolution image (e) is restored from the scanning beam contour (c) and the tilt image (d) of specimen B. On the tilt image for specimen B, a line is drawn downwards and to the left for showing beam warping due to the beam tilt, however this warping is not visible on the high resolution image (e) after the image processing. One can see that the resolution was restored and that the edges have become sharp.

Second Embodiment

Figure 4:
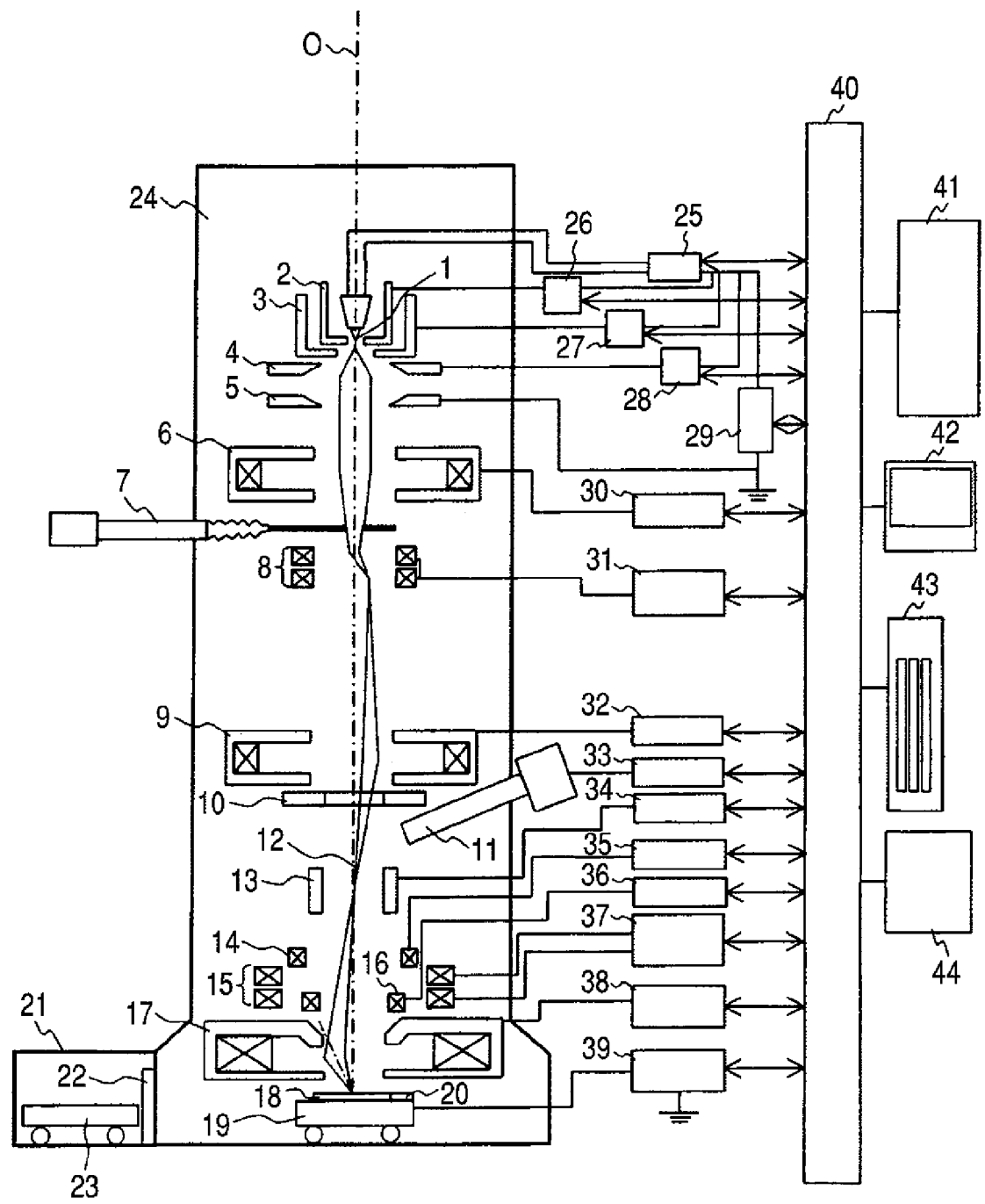
FIG. 4 is an illustration showing the critical dimension SEM serving as the observation device of the second embodiment of this invention.

The structure of the critical dimension SEM serving as the tilted illumination observation apparatus of the first embodiment of this invention is shown next in FIG. 4.

In FIG. 4, a Schottky emitter 1 is an electron supply utilizing the Schottky effect to disperse for example oxygen and zirconium into single-crystal tungsten. A suppressor electrode 2 and an extraction electrode 3 are installed in the vicinity of the Schottky emitter 1. Heating the Schottky emitter 1 and then applying a voltage of approximately +2 kilovolts across the extraction electrode 3 and Schottky emitter 1 causes it to emit Schottky electrons. A negative voltage applied to the suppressor electron 2 suppresses electrons emitted from other than the tip of the Schottky emitter 1. Electrons leaving from the hole in the extraction electrode 3 are accelerated and converged to the desired acceleration voltage by the static lens formed by the first anode 4 and the second anode 5.

Electrons that left the second anode 5 are then converged by the first condenser lens 6 in the condenser lens unit, and the current flow quantity limited by the condenser movable aperture 7. A double deflector 8 made up of a scanning unit and a scanning coil 15 tilt the beam. This double deflector 8 is here positioned beneath the first condenser lens 6, however it need not be positioned there, and may be positioned in the vicinity of the first condenser lens 6 or in the vicinity of the second condenser lens 9, or may be overlapped onto the scanning coil 15 of the scanning unit. If there is a stationary beam crossover in the optical system then a single-stage deflector may be installed in this position. The tilted beam may pass through the second condenser lens, and after crossing the position, irradiate onto a position shifted from the axis on the objective lens 17 of the objective lens unit.

If the double deflector 8 and the first and second condenser lenses 6, 9 that make up the condenser lens unit are linked at the beam crossover 12 on this optical axis 0, and set so as not to deviate (shift) during beam tilting or beam non-tilting, then an SEM image scanned by the tilt beam can be acquired within the same visual field by the converging effect of the objective lens 17 of the objective lens unit. The double deflector 8 can adjust the tilt angle and the azimuth. A tilt image can in this way be acquired at an optional tilt angle and azimuth. The absolute quantity of the tilt angle and the azimuth may be measured beforehand using a concave pyramid type specimen as shown for example in JP-A-2005-183369.

A retarding voltage power supply 39 applies a retarding voltage to the specimen stage 19, which slows down the tilt irradiation beam that is irradiated onto the specimen 18. The tilt irradiation beam is scanned by the scanning coil 15 across the specimen 18. The standard specimen 20 is mounted on a corner of the specimen stand 19.

The vacuum chamber 24 in FIG. 4 includes a beam crossover 12, an objective lens aligner 14, a stigma coil 16, a specimen preparation chamber 21, a gate valve 22, and a specimen exchange unit 23. Power is supplied to each unit in this vacuum chamber 24 by a heating power supply 25, a suppressor power supply 26, an extraction power supply 27, a high voltage power supply 28, an accelerating voltage power supply 29, a lens current supply 30, a beam deflector power supply 31, a lens current supply 32, a second electron detector power supply 33, a ExB filter power supply 34, an objective lens aligner power supply 35, a stigmator current supply 36, a scanning coil current supply 37, and a lens current supply 38.

The secondary electrons and reflected electrons emitted from the specimen by the beam scan, exit above the objective lens, reach the ExB filter 13 where their trajectories are curved, and then captured by the secondary electron detector 11 and detected as electrical signals. These electrons may alternatively strike the reflection plate 10, generate tertiary electrons there. These tertiary electrons are captured by the secondary electron detector 11 and detected as signals.

The detected signals are accumulated as image data in an external memory 41 serving as the memory unit upon receiving a command from the computer 40 serving as the control unit. The previously described tilt image and non-tilt image are accumulated in this external memory 41 as image data along with a file showing those acquisition conditions.

When the operator enters a command to the computer 40 from the console 43 serving as the entry unit, or when the file with the required conditions is checked; the computer 40 extracts the required image from the external memory 41 and, conveys that image to the image processor 44 in the image processor unit where the necessary image computations such as in (6) (8), (9), are executed, and the results output to the display unit 42 of the display unit serving as the output unit.

Figure 3:
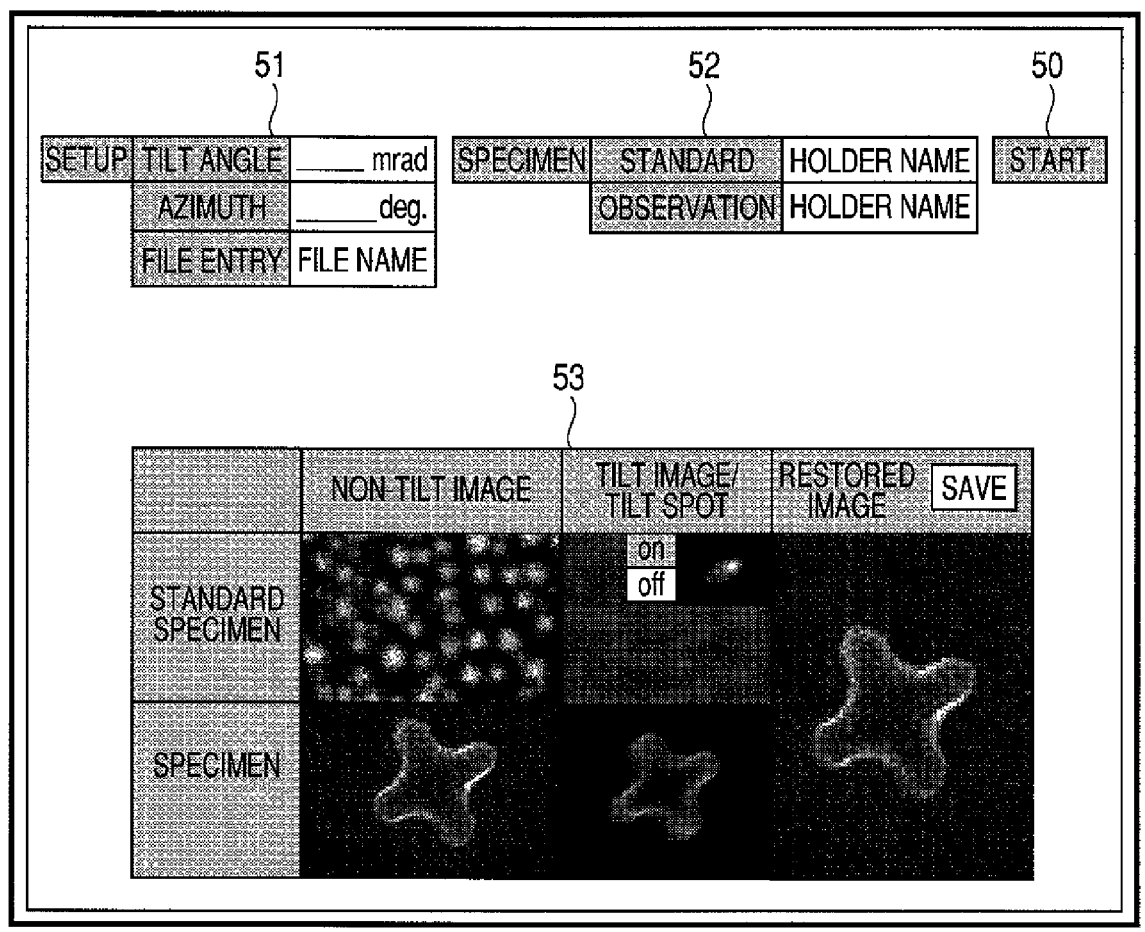
FIG. 3 is a drawing showing an example of the operating screen for operating the observation device by the observation method of the first embodiment.

FIG. 3 shows an example of the operating screen in the above described embodiment. Here it is assumed that the absolute quantity of the beam tilt angle is data measured by utilizing the device structure shown in FIG. 4 and using the concave pyramid type specimen such as disclosed in JP-A-2005-183369. Also assumed are that the correspondence with size of the coil electrical current value for the deflector forming the tilt beam is known, and that an electronic optical system capable of setting the beam tilt angle and azimuth is used.

The SEM is first of all set to a state allowing capture of an image at the desired acceleration voltage and beam current. The image is next displayed on the display unit 42 containing for example a touch panel. The setup key 51 on the upper left of the screen is then pressed and the tilt angle and azimuth of the irradiation beam are input from a pull-down menu. If there are multiple tilted illumination observation conditions then these are written as an input file in a separate operation. The file name is then specified and loaded into the computer 40.

The standard specimen is next selected from the pull-down menu via the specimen setting button 52 on the upper center part of the screen, the image is accumulated and the holder name is input. Next, the specimen stage is aligned with the standard specimen, the visual field is selected, and tasks such as magnification (or scale) focus, and astigmatism alignment performed. The start button 50 then lights up when the start button 50 on the upper right of the screen is next pressed in the same way via the touch panel, and a non-tilt irradiation image of the standard specimen is first of all acquired, and displayed on the left side of the image window 53. This image data is simultaneously accumulated into a pre-specified storage destination holder within a memory device 41. The SEM set with the pre-specified beam tilt angle and azimuth then captures the tilt irradiation image.

The image is then displayed in the center of the image window 53 on the display unit 42 serving as the display unit. This image data is also simultaneously accumulated so as to allow identification into a pre-specified storage destination holder within the memory device 41. The image processor 44 serving as the image processing unit then subjects these two image data to the image processing of STEP 7 in the embodiment in FIG. 1 under the control of the computer 40. The processing results Rt0 can then be displayed on the upper right section of this tilt irradiation image by turning the tilt SPOT button on.

At this point, the start button 50 (light) in FIG. 3 extinguishes. The observation menu is then selected from the specimen setting button 52, and the file name to accumulate the image is specified.

The specimen stage 19 is next moved to the position of the specimen for observation, and the desired field of view is selected. The magnification (or scale) is set to the same magnification as the prior standard specimen. If this magnification is different, then the software applies a restriction to prevent pressing of the next start button 50. When the start button 50 is next pressed, the acquiring and display of the non-tilt image of the specimen, and the acquiring and display of the tilt image in the same visual field are automatically performed. Finally, the processing ends with the results from the image processing of STEP 12 in FIG. 1 displayed as a restored resolution tilt image on the display unit 42. Pressing the SAVE button can accumulate the images so as to allow identification in the observation holder within the memory device 41.

The (critical dimension) CD-SEM can perform measurements such as the height of the specimen by using multiple resolution-restored tilt images obtained by the above described first embodiment using the methods disclosed in JP-A-2005-183369. Needless to say, a three-dimensional image of the specimen can be displayed by selecting an appropriate tilt angle and utilizing a dedicated three-dimensional (3D) display unit.

The above described invention is not limited to a SEM, and may for example be utilized in scanning ion microscopes, semiconductor inspection devices, and focused ion beam systems, etc.

What is claimed is:

1. A tilted illumination observation method for observing an observation specimen, comprising:
    directing a focused charged particle beam to scan a standard specimen;
    detecting reflected particles or secondary particles emitted from the standard specimen;
    obtaining a perpendicular irradiation image of the standard specimen;
    obtaining a first tilted irradiation image of the standard specimen;
    directing a focused charged particle beam to scan an observation specimen;
    detecting reflected particles or secondary particles emitted from the observation specimen;
    obtaining a second tilted irradiation image of the observation specimen under the same condition used to obtain the first tilted irradiation image;
    obtaining an image that compensates for blurring of the second tilted irradiation image by utilizing the perpendicular irradiation image and the first tilted irradiation image;
    wherein obtaining an image that compensates for blurring comprises:
    dividing a first Fourier transform of the first tilted irradiation image by a second Fourier transform of the perpendicular irradiation image to obtain a first result;
    dividing a third Fourier transform of the second tilted irradiation image by the first result to obtain a second result; and
    subjecting the second result to an inverse Fourier transform.

2. The tilted illumination observation method according to claim 1, wherein a three-dimensional shape of the observation specimen is found based on a single or multiple tilt irradiation images.

3. The tilted illumination observation method according to claim 1, wherein a three-dimensional shape of the observation specimen is found based on a single or multiple tilt irradiation images.

4. The tilted illumination observation method according to claim 1, wherein the standard specimen is gold particles or platinum particles on a flat carbon or silicon substrate.

5. The tilted illumination observation method according to claim 1, wherein the standard specimen is gold particles or platinum particles on a flat carbon or silicon substrate.

6. An observation device to observe an observation specimen by utilizing an image obtained by detecting secondary particles or reflected particles emitted from the observation specimen due to irradiating the observation specimen with a focused charged particle beam, the observation device comprising:
    a charged particle source to supply a charged particle beam;
    a condenser lens unit to control the focus position and the focus angle of the charged particle beam emitted from the charged particle source;
    an objective lens unit to converge the charged particle beam onto the observation specimen;
    a scanning unit to scan the charged particle beam onto the observation specimen at a desired tilt angle;
    an image acquisition unit to detect the secondary particles or the reflected particles emitted from the observation specimen and a standard specimen, and acquire images synchronized with the scanning by the charged particle beam;
    an image processor unit to correct blurring of an image of the observation specimen obtained with the charged particle beam during tilted irradiation, by using a first image of the standard specimen acquired by tilted irradiation and a second image of the standard specimen acquired by perpendicular irradiation; and
    a display unit to display a corrected image of the observation specimen;
    wherein the image processor unit is configured to execute processes for:
    dividing a first Fourier transform of the first image by a second Fourier transform of the second image to obtain a first result;
    dividing a third Fourier transform of the image of the observation specimen by the first result to obtain a second result; and
    subjecting the second result to an inverse Fourier transform.

7. The observation device according to claim 6, wherein gold particles or platinum particles on a flat carbon or silicon substrate are utilized as the standard specimen.

8. The observation device according to claim 6, wherein the image processor unit acquires information on the three-dimensional shape of the observation specimen based on single or multiple tilt irradiation images.

9. The observation device according to claim 6,
    wherein the condenser lens unit is composed of a first condenser lens, and a second condenser lens placed on the observation specimen side from the first condenser lens; and
    wherein the scanning unit includes a deflector unit that tilts the charged particle beam, the deflector being installed between the first condenser lens and the second condenser lens.

10. An observation device to observe an observation specimen by utilizing an image obtained by detecting secondary particles or reflected particles emitted from the observation specimen due to irradiating the observation specimen with a focused charged particle beam, the observation device comprising:
    a charged particle source to supply a charged particle beam;
    a condenser lens unit to control the focus position and the focus angle of the charged particle beam emitted from the charged particle source;
    an objective lens unit to converge the charged particle beam onto the observation specimen;
    a scanning unit to scan the charged particle beam onto the observation specimen at a desired tilt angle;
    an image acquisition unit to detect the secondary particles or the reflected particles emitted from the observation specimen and a standard specimen, and acquire images synchronized with the scanning by the charged particle beam;

an image processor unit to correct blurring of an image of the observation specimen obtained with the charged particle beam during tilted irradiation, by using a first image of the standard specimen acquired by tilted irradiation and a second image of the standard specimen acquired by perpendicular irradiation;

a display unit to display a corrected image of the observation specimen;

wherein the image processor unit is configured to execute processes for:

dividing a first Fourier transform $F[A_t]$ of the first image by a second Fourier transform $F[A_0]$ of the second image to obtain a first result;

dividing a third Fourier transform $F[B_t]$ of the image of the observation specimen by the first result to obtain a second result; and subjecting the second result to an inverse Fourier transform $F^{-1}[F[B_t]/\{F[A_t]/F[A_0]\}]$, where $A_t$ and $A_0$ respectively denote the distribution function for emission of the secondary particles or the reflected particles from the standard specimen during tilt irradiation and non-tilt irradiation; and $B_t$ denotes the distribution function for emission of the secondary particles or the reflected particles from the standard specimen during tilt irradiation.

\* \* \* \* \*